United States Patent [19]

Lee

[11] Patent Number: 4,628,938

[45] Date of Patent: Dec. 16, 1986

[54] CONTINUOUS APPLANATION TONOMETER

[76] Inventor: David A. Lee, 35 Northampton St., Boston, Mass. 02118

[21] Appl. No.: 806,311

[22] Filed: Dec. 9, 1985

[51] Int. Cl.⁴ .............................................. A61B 3/16
[52] U.S. Cl. .................................................... 128/652
[58] Field of Search .............................. 128/649–652, 128/645, 646; 73/78, 715

[56] References Cited

U.S. PATENT DOCUMENTS 3,958,560 5/1976 March .................................. 128/633

FOREIGN PATENT DOCUMENTS 7408214 6/1974 Netherlands .......................... 128/652

Primary Examiner—Kyle L. Howell
Assistant Examiner—Randy Citrin
Attorney, Agent, or Firm—Thompson, Birch, Gauthier & Samuels

[57] ABSTRACT

A non-invasive, continuous applanation tonometer for measuring intraocular pressure is disclosed. The instrument comprises a flexible contact lens which includes an inflatable applanating chamber; a reservoir of a substantially noncompressible fluid connected to the applanating chamber by a thin, flexible tube; a pump for moving the substantially noncompressible fluid between the reservoir and the applanating chamber; and a pressure transducer to measure the fluid pressure.

18 Claims, 2 Drawing Figures

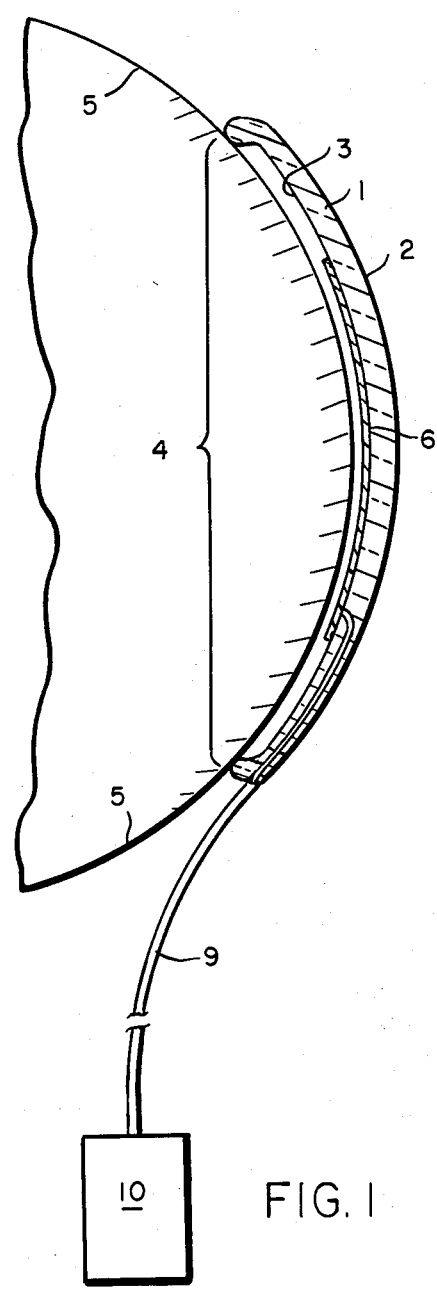
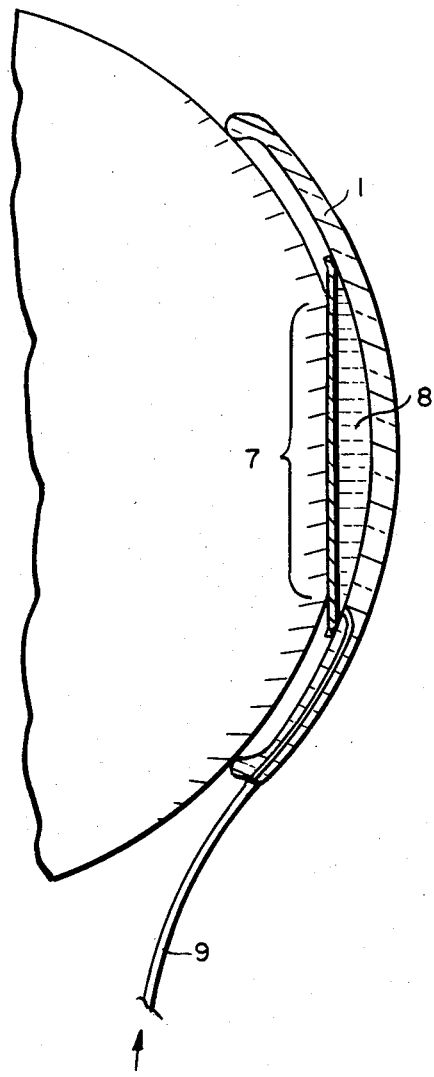
FIG. 1
FIG. 2

CONTINUOUS APPLANATION TONOMETER

BACKGROUND OF THE INVENTION

Glaucoma is a major cause of irreversible blindness in the United States. Approximately one percent of the general population has this disease. The disease is characterized by elevated intraocular pressure, optic nerve damage, and visual field loss. Symptoms of the disease may include eye pain and visual disturbances, but usually it is asymptomatic. There are many types of glaucoma, the most common type being primary openangle glaucoma. This type of glaucoma usually occurs in older people and may also have a hereditary predisposition.

Most glaucomas have elevated intraocular pressure as a major characteristic. It is therefore important to be able to measure this parameter accurately for both the diagnosis and the treatment of glaucoma. The intraocular pressure in normal people, however, varies throughout the day. It is usually highest in the early morning and lowest in the evening. The size of this fluctuation is believed to be accentuated in people with glaucoma. Therefore, an intraocular pressure measurement at a single point of time may not tell the whole story. A series of intraocular pressure readings taken at different times of the day and at night is more important in the assessment of a patient with glaucoma. A normal intraocular pressure reading in the physican's office does not rule out the possibility of a higher intraocular pressure "spike" occurring at another time at home or at work.

Intraocular pressure is usually measured with a tonometer. Clinical tonometers operate by measuring the force required to momentarily deform or depress an area on the surface of the eye and then relating this force to the intraocular pressure. These instruments are only capable of making an instantaneous or "spot" measurement of intraocular pressure. The desirability of making continuous intraocular pressure measurement, however, has been recognized and led to several efforts to design a suitable device.

One such instrument uses strain gauges mounted in soft contact lenses that sense the deformation of the meridional angle of juncture between the cornea and sclera to measure changes in intraocular pressure. These strain gauges have to be positioned exactly over the corneoscleral junction to obtain maximum output; and, the soft contact lenses have to be individually fit, molded, and calibrated for each subject's eye because of individual differences in the meridional angle of juncture.

Another instrument uses a miniature scleral applanating device that has a transensor consisting of a passive resonant coil/capacitor combination which is made pressure sensitive by the movement of a small ferrite plate which acts as its applanating surface. Oscillation induced in the transensor by a remote grid dip oscillator is monitored by a digital frequency counter. The resonant frequency of oscillation in the transensor is then linearly related to the in vitro intraocular pressure. This instrument, too, suffers from many disadvantages and drawbacks. Because of the effect on the resonant frequency of the ferrite plate, the accuracy of this instrument can vary according to temperature, atmospheric pressure, coupling of the transensor to the eye, physical properties of the sclera, mechanical instability of the transensor, permeability of the transensor to saline, and the geometric relationship between the transensor and the aerial system. The reproducibility of intraocular pressure readings between eyes over a period of time is poor. Ocular rigidity has a significant effect on the calibration curves. Calibration may be necessary for individual eyes and species.

Still another type of instrument in the prior art employs a suction cup designed to fit the periphery of the cornea and to applantate its central part. A slow, continuous saline infusion entering through a central opening forms a disc of fluid between applanating and applanated surface in which the pressure is followed by a conventional pressure transducer. The saline leaves the periphery of the cup via a hanging tube creating a suction pressure of approximately 15 mm. Hg, which keeps the cup on the cornea. This instrument is quite reproducible in its measurements, but it tends to overestimate the intraocular pressure. Also it is not very portable and the tested subject is not able to see during the pressure measurements.

In contrast with these various prior art devices, the ideal non-invasive, continuous intraocular pressure monitoring device should have the following features: (1) It must be accurate, reproducible, and independent of gravity in its measurements; (2) The tested subjects should be able to wear the device safely, comfortably, and conveniently without disturbance of vision or of rountine daily activities, including sleeping and taking any ocular medications; and (3) The device should also be simple to operate, independent of subjective judgment from the operator, and inexpensive to purchase and maintain. The instrument of this invention meets all of these important criteria.

BRIEF DESCRIPTION OF THE DRAWINGS

FIG. 1 is a schematic side view of an eye together with the contact lens, applanating chamber, fluid reservoir and connecting tube of this invention in which the applanating chamber is in its uninflated state.

FIG. 2 is a schematic side view of an eye together with this invention similar to FIG. 1 except that the applanating chamber is now shown in its fully inflated state.

FIG. 3 is a schematic perspective view of one embodiment of the invention wherein the device is integrated with a pair of conventional spectacle frames.

SUMMARY OF THE INVENTION

The continuous, non-invasive, applanation tonometer of this invention utilizes the principles of measuring the force required to flatten a pre-determined area of the surface of the eye and the physical properties that cause a contact lens to adhere to the surface of the eye.

Various factors determine the adhesion of a contact lens to the surface of an eye. Many of these variables have still not been completely characterized quantitatively. The most important factor responsible for the adhesion of a contact lens to the surface of the eye is surface tension according to the following formula:

$$P_h = P_a + \frac{\pi d\, S \sin\theta}{A}$$

where
$P_h$ = Hydrostatic pressure of the pre-corneal tear film
$P_a$ = Atmospheric pressure
$S$ = Surface tension
$d$ = Diameter of the contact lens θ = Angle made by the prelens tear film and the frontal plane of the eye
A = Area of the anterior surface of the lens.
The surface tension factor, $$\frac{\pi d \, S \sin \theta}{A},$$

is the force actually responsible for the adhesion of the contact lens to the surface of the eye. Contact lenses with greater surface areas have greater adherence to the surface of the eye by increasing "d" (the diameter of the contact lens) in the surface tension factor. Contact lenses with a steeper base curve (smaller posterior radius of curvature) also have increased adherence by increasing "θ" (the angle made by the prelens tear film and the frontal plane of the eye) in the surface tension factor. Wetting agents or agents that would increase tear film viscosity would increase the attraction of the tear molecules to the molecules of the contact lens and the surface of the eye allowing a more even spread of tears which probably aids the surface tension force "S" and increases adherence. Also various types of plastic or rubber materials used to make contact lenses may have different adhesive qualities to the tear film and ocular surface. These factors may be adjusted to maximize or minimize adhesive qualities as desired.

Depending on the position of the contact lens on the surface of the eye, gravitational force may have an effect on the adherence of the contact lens to the surface of the eye. If the contact lens is placed in the inferior, nasal, or lateral conjunctival fornix over the sclera or anteriorly over the cornea, larger and thicker lenses with greater mass may oppose the surface tension force and decrease the adherence of the contact lens to the surface of the eye. If the contact lens is placed in the superior conjunctival fornix over the sclera, the gravitational force may increase the adherence of the lens when the subject is in an upright position. If one wishes to minimize the mass of a contact lens, one can make the lens out of a less dense material. make the lens smaller in diameter or make a lens as thin as possible. In general a contact lens should be made as thin as possible for greater wearer comfort and greater adherence to the ocular surface. However, the thickness of a contact lens is limited by its edge thickness and diameter. It has been found that an edge thickness before finishing of approximately 0.12 mm is optimum.

The adherence of a contact lens to the ocular surface is also due to negative pressure (as compared with the atmospheric pressure) in the space between the lens and the ocular surface which is filled with tear fluid. The strength of the negative pressure is expressed in the equation:

$$F = \frac{2T}{x \cos \theta}$$

where
F = Negative pressure
T = Surface tension
x = The distance of the gap between the contact lens and the ocular surface
θ = Contact angle of water In order for this negative pressure to be maintained, there has to be an effective seal around the edges of the contact lens. If the radius of curvature of the ocular surface covered by the contact lens is increased, but the contact lens base curve is constant or decreased and the seal around the edges of the contact lens is effective, then the negative pressure will increase in the space between the lens and the ocular surface and, as a result, the adherence of the contact lens will increase. The greater the clearance, the more the adherence, provided the lens will allow sufficient elastic deformation. Within certain limits, the greater the elasticity of the lens, the greater will be the effect of this mechanism. The thinner the lens, the greater will be the deformation for a given pressure. The properties of elasticity and adhesion of the contact lens to the surface of the eye can be adjusted by developing and using various plastic and rubber materials of different compositions.

The eyelids may also increase the adherence of the contact lens to the ocular surface by mechanical support if the lens is placed in the conjunctival fornix (superiorly, inferiorly, temporally, or nasally) overlying the sclera.

The fundamental design for my non-invasive, continuous applanation tonometer is based on the foregoing principles of adherence of a contact lens to an ocular surface and the measurement of intraocular pressure by measuring the force that is required to flatten a defined area of the ocular surface. Briefly, the invention comprises a contact lens having a thin, ultraflexible membrane on the concave surface of the contact lens which is capable of being inflated to indent a predetermined area of the surface of the eye. The force that is required to indent this pre-determined are is directly porportional to the intraocular pressure. When the membrane is applanating the ocular surface, it is necessary that the contact lens remain adherent to the surface of the eye and not separate from the ocular surface. Otherwise, the area of the eye being applanated would be variable and this would prevent accurate intraocular pressure measurement. Based on the foregoing principles and formulas, a person skilled in the art can modify and determine the exact parameters for making and using this invention through routine experimentation.

DESCRIPTION OF THE PREFERRED EMBODIMENT

The non-invasive, continuous applanation tonometer of this invention comprises in combination the following elements: (1) a flexible contact lens which includes an inflatable applanating chamber; (2) a reservoir of a substantially noncompressible fluid; (3) connecting means for connecting the fluid reservoir to the applanating chamber; (4) pump means for moving the fluid between the reservoir and the applanating chamber; and, (5) pressure-measuring means for measuring the fluid pressure in the applanating chamber.

More particularly, as shown in the drawings, the contact lens of this invention is specially designed to maximize adherence of the lens to the ocular surface while maintaining a high level of wearing comfort following the guidelines previously discussed. In FIGS. 1 and 2, the lens 1 has an outer convex surface 2 and a concave inner ocular surface 3 which is perfectly smooth and adapted to accommodate any ocular wall since the flexibility of the contact lens material makes it possible for its inner surface (which is covered at least in part by the applanating membrane) to vary its radius of curvature. The contact lens may be positioned over either the cornea 4 of the eye or over the sclera 5. If positioned over the cornea, the contact lens material should be transparent to allow the subject wearing it to be able to see with minimal visual impairment during the intraocular pressure measurements. The contact lens may be fashioned from any conventional, flexible contact lens material such as silicone and polymethylmethacrylate.

The applanating membrane 6 is located on the concave surface 3 of the contact lens between the contact lens and the tear film on the surface of the eye. This membrane is very thin, ultraflexible, and distensible. It should be very resilient and be able to retain its original shape after repeated distensions. There should be no or minimal pressure difference across the membrane. It should be substantially circular and at least three millimeters in diameter. The optimum area is 5.5 to 6.0 millimeters in diameter. If the area flattened is too large, then the pressure within the eye will be artificially elevated. The precise dimensions for optimum results can be determined experimentally. Once the applanating membrane is fully inflated, as shown in FIG. 2, it will flatten a pre determined substantially circular area 7 of the ocular surface. At this point the pressure in the interior 8 of the applanating chamber will be equal to the intraocular pressure. As the applanating membrane inflates and applanates the surface of the eye, the radius of curvature of the ocular surface increases resulting in an increase in the negative pressure in the space that is covered by the contact lens according to the mathematical formulas set forth above. This negative pressure increases the adhesion of the contact lens to the surface of the eye and thus counteracts the force that is required for the thin membrane to applanate the surface of the eye. This feature also obviates the need for this instrument to be calibrated individually for each subject that uses it.

The preferred connecting means in accordance with this invention is a thin, flexible, and soft (for wearer comfort) tube 9 connecting the applanating chamber of the contact lens to a reservoir 10 containing a noncompressible fluid that is used to inflate the membrane. The bore of the tube should not be readily distensible radially and should maintain a substantially constant volume up to internal pressures of 50 to 60 mm. Hg.

Reservoir 10 is a chamber which holds a pre-determined volume of a fluid which is substantially noncompressible at fluid pressures up to about 60 mm. Hg. The fluid should be nontoxic to humans in small quantities in the event of a leak in the system. Such fluids include water, saline solution and many oils of both organic and petrochemical origin. A fluid with a low specific gravity is especially desirable because this will reduce the total weight of this system. The volume of the substantially noncompressible fluid is such that the volume of fluid in the reservoir is exactly enough to fully inflate the applanating chamber and flatten a portion of the ocular surface a constant and pre-determined amount. For this reason, it is important that the total volume of the system (i.e. reservoir, connecting tube and applanating chamber) remain substantially constant over a wide range of pressure, for example from zero to about 60 mm. Hg.

FIG. 3 shows the contact lens 1 of this invention integrated with a pair of conventional spectacle frames. In FIG. 3, the fluid reservoir 10, pumping means 12, and pressure-measuring and recording means 14 are attached as a single unit to one side arm of the spectacle frames. Reservoir 10 is shown connected to lens 1 by means of tube 9 as described above.

The pumping means 12 of this invention is preferably a motorized pump which can periodically fill and empty the applanating chamber at variable rates of speed and for variable periods of time. The pressure-measuring means of this invention can be any suitable pressure-sensitive device. One preferred pressure sensitive device is a conventional pressure transducer. For example, at the point when the applanating membrane chamber is completely full, the pressure in the reservoir is equal to the intraocular pressure and the reservoir can automatically be opened to a conventional pressure transducer to measure the intraocular pressure, which can further be recorded on a continuous recorder. In one variation, the pump, pressure transducer, and recorder can all be battery powered. In a further embodiment, the reservoir, pump, and pressure transducer can be attached as a single unit to a specially designed portable holder.

Many other variations and modifications of my basic design will be readily apparent to those skilled in the art, and all such variations and modifications are intended to be encompassed by this application. In particular, this instrument has many potential clinical and research applications in the diagnosis and treatment of glaucoma, and in studying the physiology of aqueous humor dynamics in humans and in other animal species in both the normal and abnormal state.

Having described my invention, what I claim is:

1. A tonometer for measuring intraocular pressure comprising a flexible contact lens having a convex and a concave side which includes an inflatable applanating chamber affixed to said concave side of said lens, a reservoir of a substantially noncompressible fluid connected to said applanating chamber, pump means for moving the noncompressible fluid between said reservoir and said applanating chamber, and pressure-measuring means for measuring the fluid pressure in said applanating chamber when said chamber is fully inflated.

2. The tonometer of claim 1 wherein said contact lens and the inflatable applanating chamber are substantially transparent.

3. The tonometer of claim 1 wherein said inflatable applanating chamber comprises a thin, flexible membrane.

4. The tonometer of claim 3 wherein said thin, flexible membrane defines a substantially circular applanating chamber of about three to six millimeters in diameter when said chamber is fully inflated.

5. The tonometer of claim 4 wherein said chamber is about 5.5 to 6.0 millimeters in diameter 6. The tonometer of claim 1 wherein said applanating chamber is connected to said reservoir by a thin, flexible tube which is not readily distensible radially and maintains a substantially constant volume at pressure up to about 50 to 60 mm. Hg.

7. The tonometer of claim 1 wherein said noncompressible fluid is selected from the group consisting of water, saline solution and oil.

8. The tonometer of claim 1 wherein a system consisting of the applanating chamber, reservoir and connecting means has a substantially constant total internal volume at internal fluid pressures ranging from zero to about 60 mm. Hg.

9. The tonometer of claim 1 wherein said pump means comprises a battery-powered motorized pump.

10. The tonometer of claim 1 wherein said pressure-measuring means comprises a battery-powered pressure transducer connected to said reservoir.

11. The tonometer of claim 10 additionally including means for continuously recording the pressure readings measured by said pressure transducer.

12. The tonometer of claim 11 wherein a system consisting of the reservoir, pump means, and pressure-measuring and recording means is attached as a single unit to a spectacle frame.

13. A method for non-invasive, continuous measurement of intraocular pressure comprising:
(a) applying a flexible contact lens which includes an inflatable applanating chamber to the surface of the eye;
(b) fully inflating said applanating chamber with a substantially noncompressible fluid so as to substantially flatten a pre-determined area of said eye surface; and,
(c) measuring the intraocular pressure by reference to the fluid pressure in said fully inflated applanating chamber.

14. The method of claim 13 wherein said contact lens is positioned over the cornea of the eye.

15. The method of claim 13 wherein said contact lens is positioned over the sclera of the eye.

16. The method of claim 13 wherein said applanating chamber is connected to a fluid reservoir having a pre-determined volume such that the non-compressible fluid in said reservoir will exactly and fully inflate said applanating chamber.

17. The method of claim 13 wherein the pressure in said fully inflated applanating chamber is measured by measuring the fluid pressure in said reservoir.

18. The method of claim 17 wherein the fluid pressure in said reservoir is continuously monitored by means of a pressure transducer connected to said reservoir and a continuous recorder connected to said pressure transducer.

* * * * *